(12) United States Patent
Tsuboi et al.

(10) Patent No.: US 6,985,777 B2
(45) Date of Patent: Jan. 10, 2006

(54) IMPLANTABLE ELECTRODE LEAD

(75) Inventors: Fuminori Tsuboi, Fujinomiya (JP); Tetsuo Tanaka, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 215 days.

(21) Appl. No.: 10/300,644

(22) Filed: Nov. 21, 2002

(65) Prior Publication Data

US 2003/0100937 A1    May 29, 2003

(30) Foreign Application Priority Data

Nov. 26, 2001   (JP) .............................. 2001-359526

(51) Int. Cl.
*A61N 1/00* (2006.01)
(52) U.S. Cl. ...................... 607/132; 607/122
(58) Field of Classification Search ......... 607/115–132
See application file for complete search history.

(56) References Cited

U.S. PATENT DOCUMENTS 4,516,584 A * 5/1985 Garcia ........................ 607/119
5,571,157 A   11/1996 McConnell
5,628,780 A * 5/1997 Helland et al. ............. 607/126
6,157,860 A   12/2000 Hauser et al.

FOREIGN PATENT DOCUMENTS

JP           8-10338 A      1/1996

* cited by examiner

*Primary Examiner*—Scott M. Getzow
(74) *Attorney, Agent, or Firm*—Buchanan Ingersoll PC

(57) ABSTRACT

An implantable electrode lead excelling in workablity during the introduction and in fastness of fixing by ligation is provided. This implantable electrode lead comprises a lubricating coat layer provided on an insulating coat over a length of at least not less than 100 mm and to a position at a distance of not more than 300 mm from the distal end of the implantable electrode lead. When this lead further comprises on the more proximal end side of the lubricating coat layer a section having regions containing a lubricating coat layer and regions containing no lubricating coat layer formed alternately therein, the workablity during the introduction can be attained and the fastness of fixing by ligation can be also secured.

4 Claims, 6 Drawing Sheets

IMPLANTABLE ELECTRODE LEAD

BACKGROUND OF THE INVENTION

1. Field of the Invention

This invention relates to an implantable electrode lead to be used in conjunction with such an implanted device as a cardiac pacemaker and a defibrillator. More particularly, it relates to a structure of an implantable electrode lead having improved operational efficiency during the course of being implanted in vivo or ligated to a vital tissue by providing at specific portions thereof with a lubricating coat layer.

2. Description of the Related Art

Numerous kinds of implantable electrode leads for the use in conjunction with such an implanted device as a cardiac pacemaker and a defibrillator have been known to the art.

The cardiac pacemaker is a device for electrically stimulating a heart directly thereby increasing a heart rate. There are two types of cardiac pacemakers, namely an external cardiac pacemaker which is disposed outside a patient body and an electrode thereof is introduced into the heart of the patient and an implanted cardiac pacemaker which itself is present in a patient body. Without reference to this classification, the cardiac pacemaker requires an implanted electrode lead to be retained in a heart or intravenously for the purpose of transmitting the electric stimulation from the cardiac pacemaker to the patient body. Thus, the implanted electrode lead is generally composed of (i) at least one electrode adapted to impart electric stimulation to a heart or detect an electric excitation of a heart, (ii) a connecting means for electrically connecting to such an implanted device as a cardiac pacemaker and a defibrillator, and (iii) a conducting part consisting of an electric conductor and an insulating coating for covering the outside of the electric conductor.

Incidentally, an implantable electrode lead to be used intravenously has a structure such that an electrode and part of a conducting part are introduced into a heart or intravenously and the conducting part and a connecting means remaining outside the vein are connected to an implanted device such as a cardiac pacemaker and a defibrillator.

A conventional implantable electrode lead in a implanted state will be described below by reference to FIG. 1. A whole length of an implantable electrode lead extends from a "proximal end" in the neighborhood of a cardiac pacemaker 10 to a "distal end" located farthest from the cardiac pacemaker 10. The proximal end comprises a connecting means for connection to the cardiac pacemaker 10 and the distal end comprises a tip electrode 40, a ring electrode 42, and the like as endocardiac electrodes besides an endocardium-fixing means 50 to be fixed to a vital tissue. A conducting part 30 which extends from the proximal end to the distal end is provided with a suturing sleeve 60 which is capable of being moved along the outer surface of the conducting part 30. For the fitting thereof, the distal end of the implantable electrode lead is introduced via a subclavian vein into a heart chamber, implanting the distal end of the lead at a proper site in the heart chamber, and fixing the tip electrode 40 and the ring electrode 42 in the heart chamber as with the endocardium-fixing means 50 or a screw for ensuring the retention at that site. Generally, at a site of the lead inserted intravenously and at a further proximal site thereof, the suturing sleeve 60 is ligated on the outer periphery thereof with a suture to fasten the conducting part 30 and the vital tissue in order to prevent the migration or elimination of the electrode.

When both the atrium and ventricle of a heart are required to be stimulated at the fitting of the implanted electrode lead, it becomes necessary to have two leads, i.e., a lead 31 for the ventricle and a lead 33 for the atrium, implanted. When these two leads are to be introduced into a small blood vessel or a tortuous blood vessel, they possibly interfere with each other to an extent of rendering the introduction difficult and they have even a possibility that the formerly implanted lead will be moved out of position by the subsequently implanted lead. This phenomenon is conspicuously observed particularly in leads which use a silicone sheath. Thus, a technique for ensuring satisfactory efficiency for the implanting work by subjecting to the surface of a conducting part such a treatment as decreasing the friction thereof has been developed. JP-A-08-10338, for example, discloses an electrode lead for the use in a cardiac pacemaker which comprises a tip electrode part, a connecting means and a conducting part having a surface coated with a hydrophilic polymer and consequently endowed with improved lubricity.

When the lubricity of the surface of the conducting part is improved by coating the surface with a hydrophilic polymer as described in JP-A-08-10338, however, although the introduction of the lead during the implantation process can be easily attained, the subsequent ligation of the lead to a vital tissue by means of a suturing sleeve entails a possibility that the suturing sleeve would slip on the conducting part to degrade the fastness of the ligation and thus the lead could not stably fixed in a body. As a result, there is also a possibility that the electrode would be randomly moved or even slipped out to render the pacing and the sensing imperfect. This adverse effect results in harming the performance which the implanted device such as a cardiac pacemaker or a defibrillator ought to manifest inherently.

This invention is directed toward realizing an implantable electrode lead which can manifest lubricity enough to introduce the implantable electrode lead and be fixed for a long time even in the case of the ligation of the lead to a vital tissue, and thus permits the stable transmission of an electric signal from the implanted device to the vital system.

SUMMARY OF THE INVENTION

The present inventors have made a detailed study on an implantable electrode lead to be used in conjunction with such an implanted device as a cardiac pacemaker and a defibrillator, to find that by imparting lubricity only to specific portions of a conducting part, the lead excels in the workability in the introduction thereof, also excels in the workability in the ligation thereof to a vital tissue via a suturing sleeve because an insulating coat in contact with an inner surface of the suturing sleeve is not provided with a lubricating coat layer, and thus the lead can be fixed on the vital tissue with high stability for a long time. This invention has been perfected based on this discovery.

To be specific, the task as described above can be accomplished by an implantable electrode lead which comprises a distal end having at least one electrode; a proximal end having a connecting means with an implanted device; a conducting part formed of an electric conductor for transmitting an electric signal between the electrode at the distal end and the connecting means at the proximal end and an insulating coat for covering the outer surface of the electric conductor; and a suturing sleeve capable of being moved along the outer surface of the insulating coat, wherein the insulating coat is provided with a lubricating coat layer on the outer surface thereof over a length of at least not less than 100 mm and to a position at a distance of not more than 300 mm from the distal end.

According to this invention, by defining the range of the lubricating coat part to be applied to the surface of the conducting part, it is made possible to provide such an implantable electrode lead as to be designed so as to excel in the workability in the introduction and to secure the stable fixing by suturing.

DESCRIPTION OF THE PREFERRED EMBODIMENTS

The first aspect of this invention relates to an implantable electrode lead which comprises a distal end having at least one electrode; a proximal end having a connecting means with an implanted device; a conducting part formed of an electric conductor for transmitting an electric signal between the electrode at the distal end and the connecting means at the proximal end and an insulating coat for covering the outer surface of the electric conductor; and a suturing sleeve capable of being moved along the outer surface of the insulating coat, wherein the insulating coat is provided with a lubricating coat layer on the outer surface thereof over a length of at least not less than 100 mm and to a position at a distance of not more than 300 mm from the distal end. According to this invention, there is provided an implantable electrode lead to be designed so as to avoid succumbing to a restriction regarding the degree with which the lubricity of the surface of the conducting part is improved by application of a coat thereon and to maintain the function of fixing by ligation at a fixing site in the suturing sleeve. Further, according to this invention, it is made possible by defining the range of the lubricating coat part to be applied to the surface of the conducting part to provide such an implantable electrode lead as avoid succumbing to a restriction regarding the degree with which the surface of the conducting part is covered with a lubricating coat and keep from impairing the function of fixing by ligation at a fixing site in the suturing sleeve.

Figure 1:
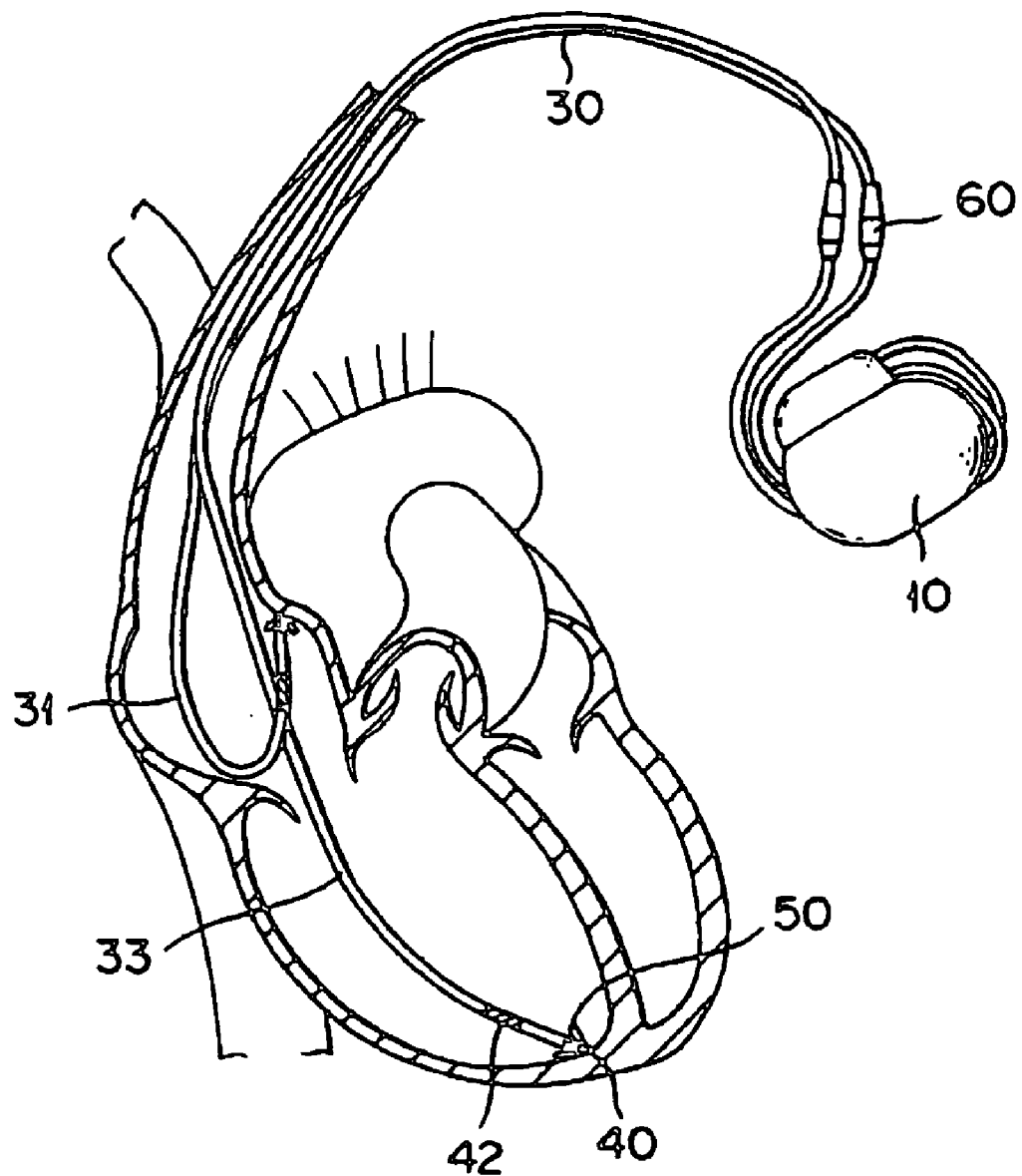
FIG. 1 is a schematic diagram illustrating two implantable electrode leads to be introduced and implanted in each of a ventricle and an atrium.
Figure 2:
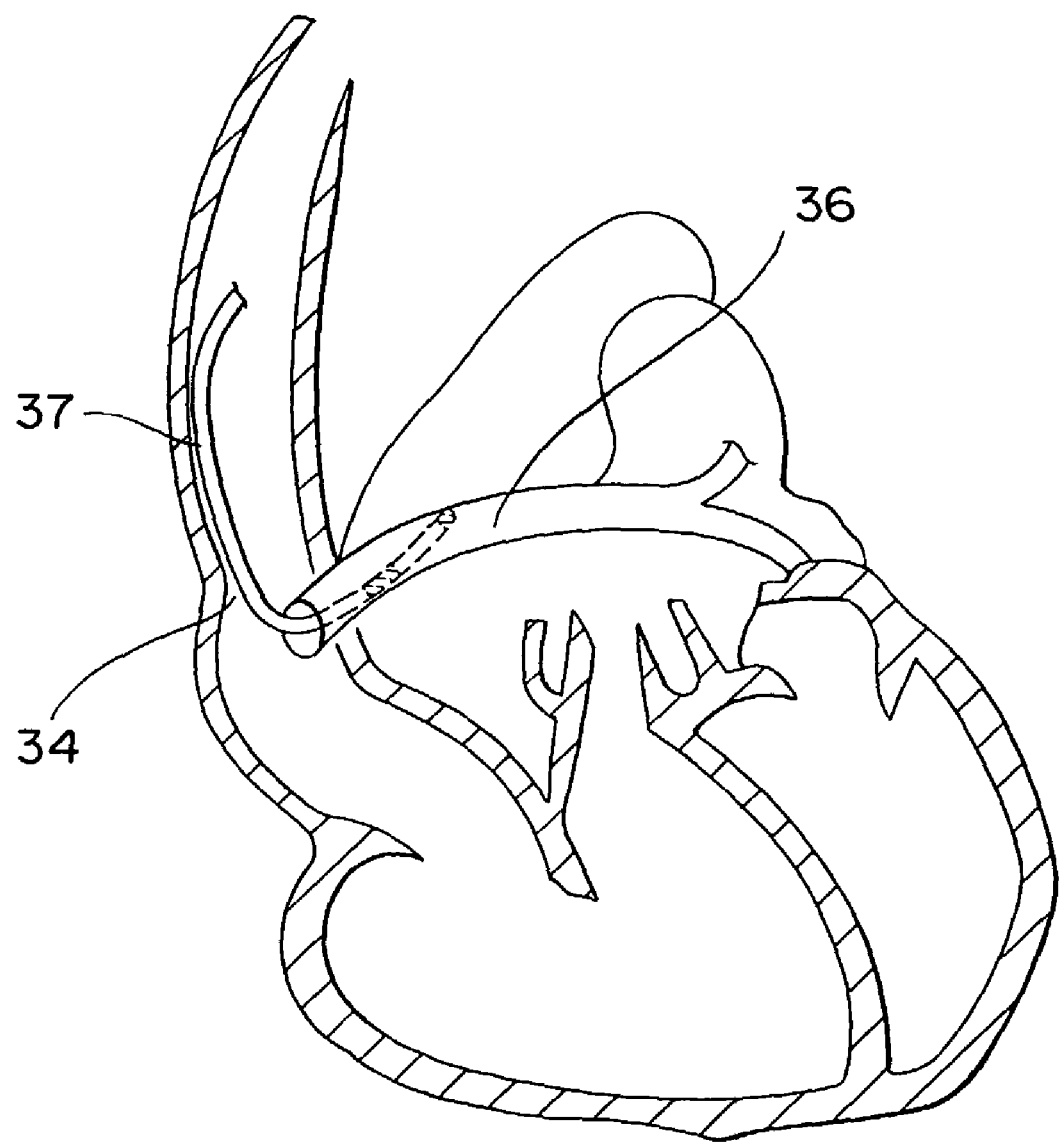
FIG. 2 is a schematic diagram illustrating an implantable electrode lead to be introduced and implanted in a coronary sinus (CS).

Further, since this invention imposes no restriction on a part in which an operator takes hold of the lead (the proximal part) regarding the degree of a lubricating coat (i.e., the proximal part is not slipped off), this invention enables to maintain efficiency in the work of effecting forced insertion at the proximal part and transmission of toque. Accordingly, when the lead is introduced into such a vessel as coronary sinus (CS) 36 which has a small diameter and has a branching as shown in FIG. 2, the vessel can be smoothly selected even in the branching part and the manipulation of the lead in the small vessel excels in the efficiency.

Now, one preferred embodiment of the implantable electrode lead contemplated by this invention will be described below with reference to FIG. 3.

Figure 3:
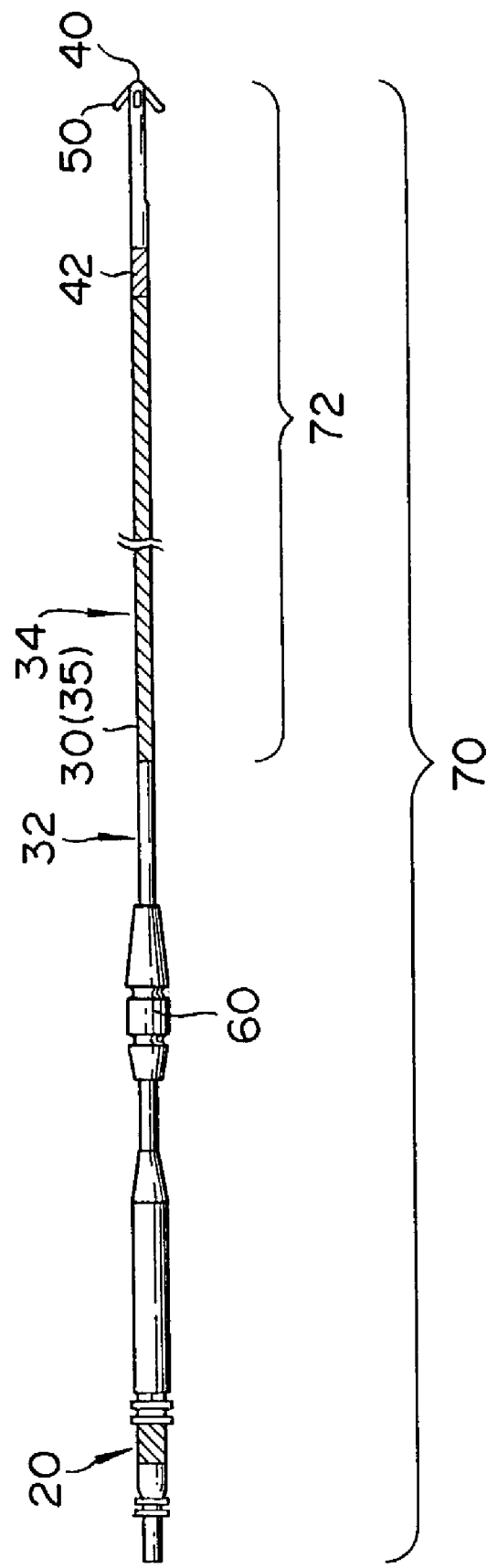
FIG. 3 is a schematic diagram illustrating an entire implantable electrode lead of this invention provided in a prescribed portion thereof with a lubricating coat layer.

The implantable electrode lead of this invention is composed of a distal end having an endocardium-fixing means 50, a proximal end having a connecting means 20 with an implanted device, and a conducting part 30 which extends from the distal end to the proximal end, as shown in FIG. 3. The distal end is further provided with at least one electrode such as a tip electrode 40, a ring electrode 42, and the like. The conducting part 30 contained therein an electric conductor which permits the transmission of an electric signal between the electrode and the connecting means 20. Then, the outer surface of the electric conductor is covered with an insulating coat 35. When the insulating coat is provided with a suturing sleeve 60 capable of moving along the outer surface thereof, the conducting part 30 can be ligated to a vital tissue by means of this suturing sleeve 60 and, therefore, can be prevented from suffering such damage as may be possibly inflicted thereon in consequence of direct ligation. This invention allows a tip electrode, a ring electrode, a connecting means, a conducting part, and a suturing sleeve which are annexed to the implantable electrode lead to be selected from relevant components which have been heretofore known to the art.

As the material for the insulating coat 35, a polymeric material may be preferably used. As typical examples of the polymeric material which proves particularly favorable, silicone, fluorosilicone, fluorine type elastomers, and polyurethane may be cited. The insulating coat made of such a polymeric material is at an advantage in manifesting excellent chemical stability when implanted for a long time and permitting the easy provision of a lubricating coat layer on the outer surface thereof.

This invention has one feature in providing a lubricating coat layer 34 on the surface of the insulating coat 35 over a length of at least not less than 100 mm and to a position at a distance of not more than 300 mm from the distal end. If the lubricating coat layer is provided over the entire length of the implantable electrode lead, it would be deficient in the fixing property to be manifested during the course of ligation. Conversely, if the lubricating coat layer is absent throughout the entire length of the implantable electrode lead, the lead would be deficient in the workability during the introduction of the lead.

In this invention, the lubricating coat layer 34 is provided within a defined range 72 at a distance of not more than 300 mm, preferably in the range of 200 to 300 mm, from the distal end. The lubricating coat layer 34 thus provided within this range 72 corresponds to a proportion in the range of 40 to 60% of an entire length 70 of the lead. So long as the lubricating coat layer 34 is provided within the range 72 based on a in vivo distance of the lead fixed in an atrium or a ventricle, the suturing sleeve 60 is present on an uncoated layer part 32 of the conducting part 30 when the implantable electrode lead is fixed by ligation in vivo. Hence, the fixing force exerted by the ligation on the implantable electrode lead cannot be degraded. Further, as far as this range 72 is duly observed, since a part in which an operator takes hold of the lead (the proximal part) is not covered with the lubricating coat layer and thus the efficiency in the work of effecting forced insertion and transmission of toque can be maintained, the operation at the proximal part can be infallibly transmitted to the lead. As a result, the excellent workability can be attained particularly when the lead is introduced into a vessel such as coronary sinus (CS) 36 which has a small diameter and has a branching.

For the purpose of smoothly introducing the lead into an organ or a vital tissue without any damage thereon, the lubricating coat layer 34 extends over a length of at least not less than 100 mm, preferably in the range of 150 to 300 mm, and particularly preferably in the range of 200 to 250 mm including a position within the defined range 72 as mentioned above.

This invention allows the lubricating coat layer 34 to be disposed at an arbitrary position so long as this position falls in the range of not more than 300 mm from the distal end in the entire length 70 of the implantable electrode lead. Since the distal end of this lead often has a tip electrode 40, an endocardium-fixing means 50, and a ring electrode 42, the lubricating coat layer 34 may be preferably formed on a part excluding these accessorial components. That is, this invention can omit the formation of the lubricating coat layer between the tip electrode 40 and the ring electrode 42. Generally, the endocardium-fixing means 50 is interposed between the tip electrode 40 and the ring electrode 42 and this means 50 is formed of a material different from the material of the insulating coat 35. In this case, the complete assembly may be attained efficiently after the insulating coat 35 on the conducting part 30 has been furnished with the lubricating coat layer 34. The additional interposition of a lubricating coat layer between the tip electrode 40 and the ring electrode 42 entails a demerit of adding to the number of steps because it requires a step of applying such a coating also to the means 50. Meanwhile, the distance between the two electrodes affects the implanting workability only a little because of a very short length as compared with the length of the lubricating coat layer 34. When the implanting workability is not affected significantly, the lubricating coat layer 34 between the two electrodes may be safely omitted. This rule, however, does not apply to a single pass lead which is provided with two or more ring electrodes or to a single electrode lead which is devoid of a ring electrode. Generally, the distance between the tip electrode 40 and the ring electrode 42 is in the range of 10 to 30 mm. When the distance falls within this range, the absence of a lubricating coat layer 34 on the insulating coat affects the implanting workability only sparingly.

Since this invention does not impose any restriction regarding the method for producing the lead, the complete assembly of the lead may precede the provision of the lubricating coat layer. In this case, the treatment for applying a lubricating coat may be carried out after a part such as a surface of an electrode which does not welcome application of a lubricating coat has been duly masked and the provision of the lubricating coat layer 34 between the tip electrode 40 and the ring electrode 42 is convenient to accomplish.

In this invention, the lubricating coat layer 34 may be prepared with a hydrophilic polymer such as a natural water-soluble polymer of a plant origin or an animal origin, a semi-synthetic water-soluble polymer, or a synthetic water-soluble polymer. As typical examples of the hydrophilic polymer, polyvinyl pyrrolidone, acrylate polymers, ethylene vinyl alcohols such as polyvinyl alcohol and polyvinyl methyl ether, polyethylene glycol, cellulose derivatives such as cellulose, methyl cellulose, and hydroxypropyl cellulose, saccharides such as mannan, chitosan, Cyamoposis Gum, xanthane gum, gumarabic, glucose, and sucrose, amino acids such as glycin, gelatin, and serine and the derivatives thereof, and natural substances such as polylactic acid, sodium alginate, and casein may be cited. In this invention, polyvinyl pyrrolidone and acrylate polymers may be preferably used because they excel in compatibility with the insulating coat 35 and in the efficiency of application.

For the formation of the lubricating coat layer 34 on the insulating coat 35, when the insulating coat 35 is formed of silicone, for example, the lubricating coat layer 34 can be conveniently formed by fixing on the insulating coat 35 a polymer having lubricity by a method of graft polymerization initiated with plasma. The formation may be otherwise effected by introducing into the insulating coat 35 a polymer having a reactive group by a method of graft polymerization initiated with plasma and then coating a polymer having lubricity to react with the reactive group to manifest lubricity. A maleate based polymer or such a polymer as gelatin may be used in place of the acrylate polymer on the condition that it is capable of fixing the polymer having lubricity on the coat.

This invention has a feature in having the lubricating coat layer 34 formed within the defined range 72 as mentioned above. This feature, however, is not meant to prohibit the lubricating coat layer from being formed on any other part on the entire length of the implantable electrode lead. It may be rather preferable to form on the more proximal end side of the lubricating coat layer a section having regions containing a lubricating coat layer and regions containing no lubricating coat layer alternately. This particular mode will be described below with reference to FIG. 4.

Figure 4:
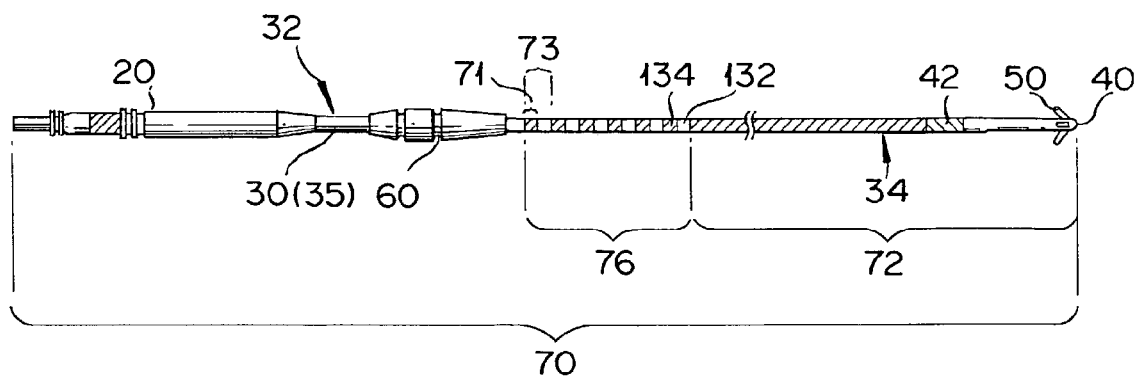
FIG. 4 is a schematic diagram illustrating an entire implantable electrode lead of this invention provided in prescribed portions thereof with a lubricating coat layer in such a manner as that the regions containing such a lubricating coat layer and the regions containing no lubricating coat layer may alternate with each other.

First, the reference numerals used in FIG. 4 equal those used in FIG. 3. The difference of FIG. 4 from FIG. 3 resides in the fact that a section 76 in which regions 134 containing a lubricating coat layer and regions 132 containing no lubricating coat layer are formed alternately is provided on the proximal end side at a distance exceeding 300 mm from the distal end. The prescribed section 76 as mentioned above is allowed to reach a neighborhood of the connecting means 20 so long as the distance from the distal end exceeds 300 mm. The preferred length of the section 76 is in the range of 50 to 300 mm. The pitch of sequentially arranged coats and the width of each of the coats are closely related to the intervals between the plurality of ligating parts formed on the suturing sleeve and this relation will be described below with reference to FIG. 5.

Figure 5:
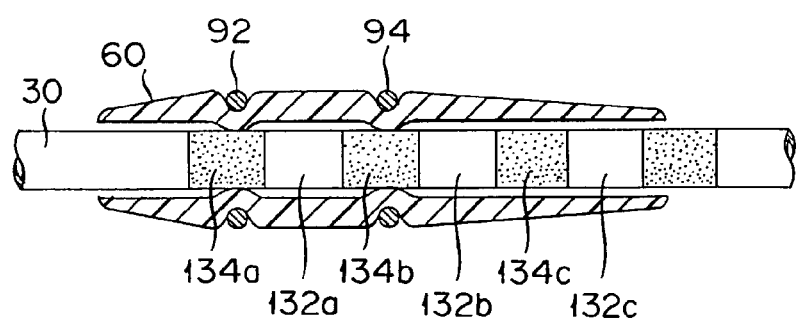
FIG. 5 is a diagram illustrating a state of ligation between a conducting part and a suturing sleeve of an implantable electrode lead in an area having regions containing a lubricating coat layer and regions containing no lubricating coat layer alternate with each other.
Figure 6:
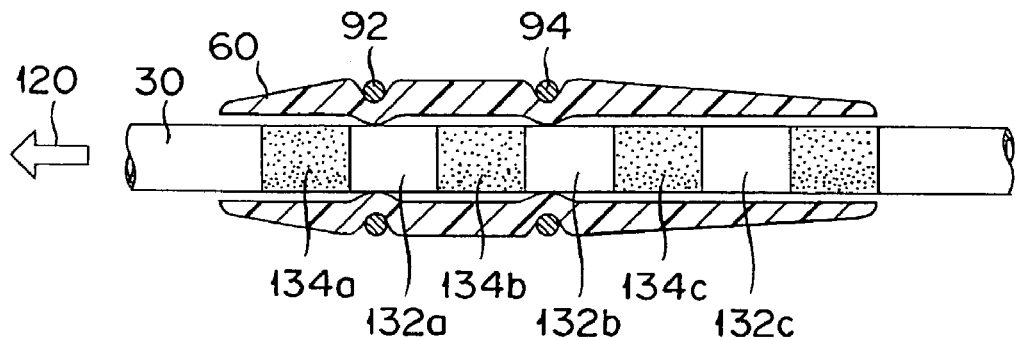
FIG. 6 is a diagram illustrating a state which the ligating part assumes after the ligating part in the state as illustrated in FIG. 5 has been varied by application of a tensile force to the conducting part.
Figure 7:
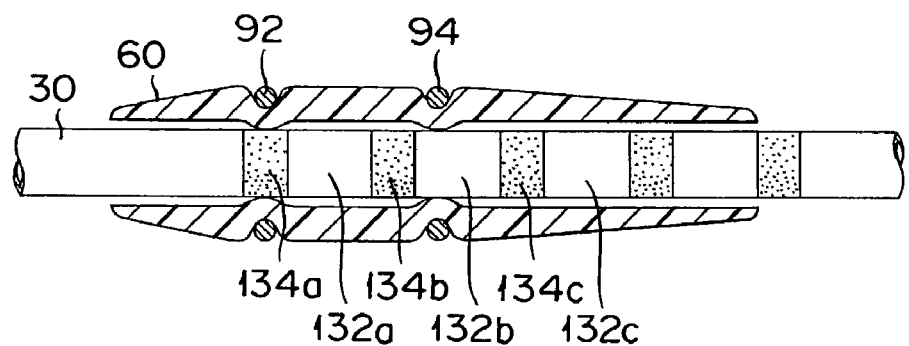
FIG. 7 is a diagram illustrating a state of ligation between a conducting part and a suturing sleeve of an implantable electrode lead where either one of a plurality of ligating parts in the suturing sleeve is present in a region containing a lubricating coat layer while the others are present in regions containing no lubricating coat layer.
Figure 8:
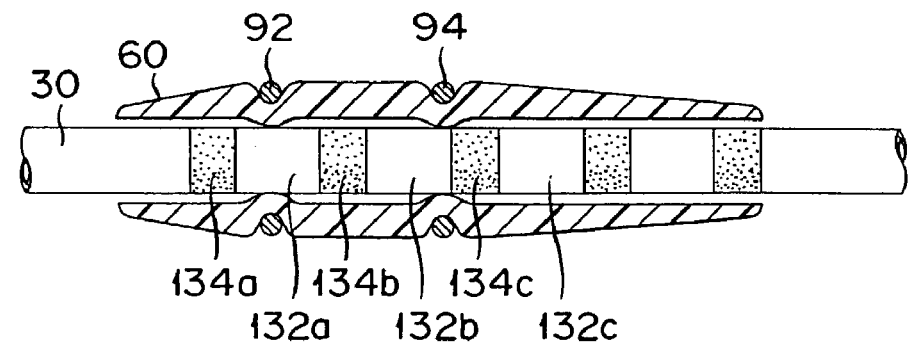
FIG. 8 is a diagram illustrating a state of ligation between a conducting part and a suturing sleeve of an implantable electrode lead where all of a plurality of ligating parts in the suturing sleeve are present in regions containing no lubricating coat layer.

FIG. 5 is a cross section of the suturing sleeve 60 which is provided on the conducting part 30 of the implantable electrode lead. The conducting part 30 is provided with regions 134a, 134b, and 134c which contain a lubricating coat layer and regions 132a, 132b, and 132c which contain no lubricating coat layer and the suturing sleeve 60 is provided with ligating parts 92, 94 which are each formed of a depression. Further, the ligating part 92 is located in a lubricating coat region 134a and the ligating part 94 is positioned in a lubricating coat region 134b. When the inner sides of the ligating parts 92, 94 of the suturing sleeve 60 in contact with the conducting part 30 respectively contact the regions 134 of the conducting part 30 containing a lubricating coat layer, the suturing sleeve 60 can be freely moved on the lubricating coat layer in spite of the ligation. The state which the suturing sleeve 60 in this arrangement assumes in consequence of the application of a tensile force 120 thereto is shown in FIG. 6. If the tensile force 120 exceeds a fixing power which can retained the conducting part 30 at each the lubricating coat part, the excess would result in giving rise to slippage between the suturing sleeve 60 and the conducting part 30. When the ligating parts 92, 94 reach regions 132a, 132b which contain no lubricating coat layer, the fixing force is exalted enough to retain the fixed state. Even when either of the ligating parts 92, 94 of the suturing sleeve 60 exists in the region 134 containing a lubricating coat layer and the remainder thereof exists in the region 132 containing no lubricating coat layer, the fastness by ligation can be ensured. This situation will be described below with reference to FIG. 7. FIG. 7 is a diagram depicting an embodiment wherein the ligating part 92 is positioned in the lubricating coat region 134a and the ligating part 94 is positioned in the region 132b containing no lubricating coat. In the ligating part 94, the fastness of fixing the conducting part 30 and the suturing sleeve 60 can be secured because the ligation is made in a part containing no lubricating coat layer. When the ligating parts 92, 94 are both positioned in the regions 132 containing no lubricating coat layer as shown in FIG. 8, these two ligating parts suffice to ensure satisfactory fastness of fixing. The pitch 73 for the coats formed in the section 76 of the conducting part 30 is preferably in the range of 1 to 15 mm and more preferably in the range of 2 to 10 mm and the width 71 of each of the coats is preferably in the range of 0.5 to 14 mm and more preferably in the range of 1 to 9 mm. Even when the positions of the lead to be fixed by ligation are more or less differentiated by such reasons as difference in physique of patients, the ligations made in the prescribed section 76 can produce a satisfactory fixing force. When the suturing sleeve 60 is positioned in the prescribed section 76, the fixation by ligation is carried out without fail in an uncoated region and consequently the fastness of fixing the conducting part 30 with the suturing sleeve 60 can be maintained.

Incidentally, the suturing sleeve does not need to be limited to having ligating parts formed at two positions. A suturing sleeve having a ligating part at one position and a suturing sleeve having ligating parts one each at three positions or more may be used instead.

The implantable electrode lead of this invention does not need to be limited to the use in a cardiac pacemaker or an implanted defibrillator. This invention can be applied to varying kinds of implantable electrode leads such as a screw-in type lead, a J type lead for an atrium, a single pass VDD lead, a single pass DDD lead, a lead for coronary sinus (CS lead), and a single electrode type lead.

EXAMPLES

Now, this invention will be described more specifically below with reference to working examples thereof.

Example 1

Figure 9:
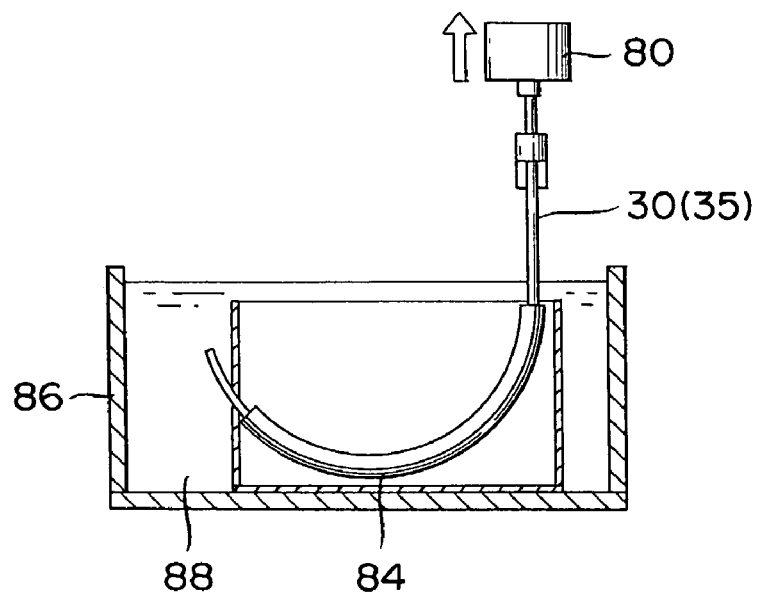
FIG. 9 is a schematic diagram illustrating a device used in Example 1 for measuring resistance against extraction.

For each of a conducting part 30 provided with an insulating coat and a conducting part 30 similarly provided with an insulating coat which was further provided thereon with a lubricating coat layer, resistance against extraction was measured with a device illustrated in FIG. 9.

As shown in FIG. 9, one end of each of the conducting parts 30 was fixed to a load cell 80 and the other end thereof was inserted into a tube 84 of ETFE measuring 3.3 mm in inside diameter and 240 mm in length, curved with a radius of curvature of 88 mm over the entire length thereof which has been immersed in a water tank 86 filled with water 88. While the conducting part 30 thus lodged in the tube was extracted from the tube, the maximum resistance offered against the extraction was measured. The insulating coat was formed of silicone and the lubricating coat layer was formed of polyvinyl pyrrolidone. The test was performed up to three repetitions on each of the conducting parts 30. The results are shown in Table 1 below.

TABLE 1

| Outer surface of conducting part | Resistance against extraction (average ± SE) |
|---|---|
| Insulating coat | 3.55 ± 0.29 (N) |
| Lubricating coat layer | 0.02 ± 0.00 (N) |

Example 2

A conducting part 30 provided with an insulating coat and a conducting part 30 similarly provided with an insulating coat which was further provided thereon with a lubricating coat layer were each subjected to ligation. The fixing force produced consequently was measured with a device as shown in FIG. 10.

Figure 10:
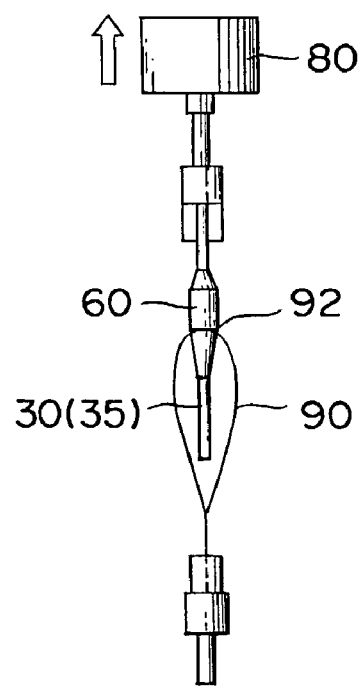
FIG. 10 is a schematic diagram illustrating a device used in Example 2 for measuring fixing force.

As shown in FIG. 10, one end of each of the conducting parts 30 was fixed to a load cell 80, ligated from the outer periphery of a ligating part 92 of a suturing sleeve 60 with a force of 18N using a suture 90 (1-0 size, silk), and kept immersed in physiological saline at 37° C. for 10 days. Subsequently, the conducting part 30 and the suture 90 used for ligation were each chucked and tested for tensile strength to measure a fixing force. The insulating coat was formed of silicone and the lubricating coat layer was formed of polyvinyl pyrrolidone. The test was performed up to three repetitions on each of the samples. The results are shown in Table 2 below.

TABLE 2

| Outer surface of conducting part | Fixing force (average ± SE) |
|---|---|
| Insulating coat | 4.71 ± 0.71 (N) |
| Lubricating coat layer | 2.83 ± 0.29 (N) |

(Results)

From the results of Example 1 and Example 2, it can be confirmed that the provision of a lubricating coat layer could secure due efficiency of operation during the course of implantation in vivo and the partial provision of a part containing no lubricating coat layer could secure due fastness of fixing by ligation. Particularly when the ligation of the conducting part 30 and a vital tissue was performed by means of a suturing sleeve 60, the conducting part 30 in contact with the inner surface of the suturing sleeve 60 could secure the fastness of fixing in the absence of a lubricating coat layer.

Example 3

An implantable electrode lead having a total length of 520 mm and constructed as shown in FIG. 4 was manufactured. This lead was composed of a connecting means 20, a conducting part 30, a tip electrode 40, and a ring electrode 42. An insulating coat 35 for this lead was formed of silicone. This lead comprised a polyvinyl pyrrolidone coat as a lubricating coat layer 34 which extends over 200 mm in length from the ring electrode 42 toward the proximal end and a section 76 of a total length of 100 mm extending over a distance of 300 mm from the ring electrode 42 and continuing into the lubricating coat layer 34 and having regions 132 containing no lubricating coat layer and regions 134 containing a lubricating coat layer formed alternately therein. The pitch 73 of coats was set to be 4 mm and the coat width 71 was set to be 2 mm. The distance between the ligating parts 92 and 94 on the suturing sleeve 60 was set to be 4 mm.

During the ligation of the lead, the suturing sleeve 60 was moved to the section 76. When it was ligated with a suture via the ligating parts 92 and 94 of the suturing sleeve 60, it assumed the state as shown in FIG. 5. When the conducting part 30 was pulled toward the proximal end, the maximum distance of slip between the conducting part 30 and the suturing sleeve 60 equaled the coat pitch 73, with the result that the state as shown in FIG. 6 was assumed and the ligation was fixed.

Example 4

A lead was manufactured by following the procedure of Example 3 while changing the coat pitch in the section 76 to 2.5 mm and also changing the coat width to 1 mm. During the ligation of the lead, the suturing sleeve 60 was moved to the section 76. When it was ligated with a suture via the ligating parts 92 and 94 of the suturing sleeve 60, it assumed the state in which the ligating part 92 was positioned in the region 134a containing a lubricating coat layer and the ligating part 94 was positioned in the region 132b containing no lubricating coat layer, as shown in FIG. 7. Since the ligation was made in an uncoated region, the fastness of fixing of the conducting part 30 and the suturing sleeve 60 could be secured. When the ligation was unknotted and was formed at a separate position, the conducting part 30 and the suturing sleeve 60 could be fixed with due fastness because the ligating part 94 was positioned in the region 132b containing no lubricating coat layer and the ligating part 92 is also positioned in the region 132a containing no lubricating coat layer, as shown in FIG. 8.

The entire disclosure of Japanese Patent Application No. 2001-359526 filed on Nov. 26, 2001 including specification, claims, drawings, and summary are incorporated herein by reference in its entirety.

What is claimed is:

1. An implantable electrode lead which comprises a distal end having at least one electrode; a proximal end having a connecting means; a conducting part formed of an electric conductor for transmitting an electric signal between said electrode at the distal end and said connecting means at the proximal end and an insulating coat for covering the outer surface of said electric conductor; and a suturing sleeve capable of being moved along the outer surface of said insulating coat, wherein said insulating coat is provided with a lubricating coat layer on the outer surface thereof over a length of at least not less than 100 mm and to a position at a distance of not more than 300 mm from said distal end, the lubricating coat layer is in the range of 40 to 60% of an entire length of the lead.

2. An implantable electrode lead according to claim 1, which further comprises on the more proximal end side of said lubricating coat layer a section having regions containing a lubricating coat layer and regions containing no lubricating coat layer formed alternately therein.

3. An implantable electrode lead according to claim 1, wherein said lubricating coat layer is formed of a hydrophilic polymeric material.

4. An implantable electrode lead according to claim 3, wherein said hydrophilic polymeric material is polyvinyl pyrrolidone (PVP).

* * * * *